US006656684B1

United States Patent
Sandler (10) Patent No.: US 6,656,684 B1
(45) Date of Patent: Dec. 2, 2003

(54) METHOD FOR PREDICTING TUMOR RECURRENCE

(75) Inventor: Anthony D. Sandler, Coralville, IA (US)

(73) Assignee: University of Iowa Research Foundation, Iowa City, IA (US)

( * ) Notice: Subject to any disclaimer, the term of this patent is extended or adjusted under 35 U.S.C. 154(b) by 76 days.

(21) Appl. No.: 09/705,146

(22) Filed: Nov. 2, 2000

(51) Int. Cl.[7] .................... C12Q 1/68; C12P 19/34; C07H 21/02; C07H 21/04

(52) U.S. Cl. ................... 435/6; 435/91.1; 435/91.2; 536/23.1; 536/24.3; 536/24.31

(58) Field of Search ........................ 435/6, 91.1, 91.2, 435/183, 810; 536/23.1, 24.3, 24.33

(56) References Cited

U.S. PATENT DOCUMENTS 6,001,962 A * 12/1999 Ramer et al. ............... 530/324
6,077,709 A *  6/2000 Bennett et al. ............. 435/375
6,103,237 A    8/2000 Saedi et al. .............. 424/185.1

OTHER PUBLICATIONS

Swana et al., "Tumor Content of the Antiapoptosis Molecule Survivin and Recurrence of Bladder Cancer," New England Journa of Medicine, Aug. 5, 1999, vol. 341, No. 6, p. 452–3.*
Sarela et al., "Expression of the antiapoptosis gene, survivin, predicts ddeath from recurrent colorectal carcinoma," Gut, vol. 46, No. 5, May 2000, pp. 645–650, abstract only.*
Adida et al., The Lancet, vol. 351, Mar. 21, 1998, pp. 882–883.*
Ambrosini et al., Nature Medicine, vol. 3, No. 8, Aug. 1997, pp. 917–921.*

Adida, C., et al., "Anti–apoptosis gene, survivin, and prognosis of neuroblastoma", *The Lancet, 351*, pp. 882–883, (1998).
Ambrosini, G., et al., "A novel anti-apoptosis gene, survivin, expressed in cancer and lymphoma", *Nature Medicine, 3 (8)*, pp. 917–921, (1997).
Ashkenazi, A., et al., "Death Receptors: Signaling and Modulation", *Science, 281 (5381)*, pp. 1305–1308, (1998).
Breslow, N., et al., "Epidemiology of Wilms Tumor", *Medical and Pediatric Oncology, 21 (3)*, pp. 172–181, (1993).
Brodeur, G.M., et al., "Neuroblastoma", *In: Principles and Practice of Pediatric Oncology*, Chapter 29, pp. 761–797, (1997).
Deveraux, Q.L., et al., "X–Linked IAP is a Direct Inhibitor of Cell–Death Proteases", *Nature, 388 (6639)*, pp. 300–304, (1997).
Donaldson, S.A., et al., "Expression of Fas/APO–1 by different clinical stages of human neuroblastoma", *Proceedings of the American Association for Cancer Research, 40*, Abstract No. 1141, p. 171, (Mar. 1999).
Li, F., et al., "Control of apoptosis and mitotic spindle checkpoint by survivin", *Nature, 396*, pp. 580–584, (1998).
Li, F., et al., "Pleiptropic cell–division defects and apoptosis induced by interference with survivin function", *Nature Cell Biology, 1 (8)*, pp. 461–466, (1999).
Liston, P., et al., "Supression of apoptosis in mammalian cells by NAIP and a related family of IAP genes", *Nature, 379*, pp. 349–353, (1996).
Lowry, O.H., et al., "Protein Measurement With The Folin Phenol Reagent", *The Journal of Biological Chemistry, 193*, pp. 265–275, (1951).

(List continued on next page.)

Primary Examiner—B. L. Sisson
(74) Attorney, Agent, or Firm—Schwegman, Lundberg, Woessner & Kluth, P.A.

(57) ABSTRACT

The present invention provides methods and kits for predicting recurrence of tumor or cancer in a mammal by calculating the ratio of the amount of Survivin and the amount of PAF in a physiological sample.

14 Claims, 7 Drawing Sheets

OTHER PUBLICATIONS

Lu, C., et al., "Expression of a Novel Antiapoptosis Gene, Survivin, Correlated with Tumor Cell Apoptosis and p53 Accumulation in Gastric Carcinomas", *Cancer Research, 58* (*9*), pp. 1808–1812, (1998).

Miller, L.J., et al., "Apoptosis", *Science, 281* (*5381*), p. 1301, (1998).

Sandler, A., et al., "Survivin in Apoptosis and Solid Tumors of Childhood", *Surgical Forum, 85th Annual Clinical Congress, vol. L*, pp. 571–572, (1999).

Swana, H.S., et al., "Tumor Content of the Antiapoptosis Molecule Survivin and Recurrence of Bladder Cancer", *The New England Journal of Medicine, 341* (*6*), pp. 452–453, (1999).

Takamizawa, S., et al., "Differential Apoptosis Gene Expression in Pediatric Tumors of the Kidney", *Journal of Pediatric Surgery, 35* (*2*), pp. 390–395, (Feb. 2000).

Tamm, I., et al., "IAP–Family Protein Survivin Inhibits Caspase Activity and Apoptosis Induced by Fas (CD95), Bax, Caspases, and Anticancer Drugs", *Cancer Research, 58* (*23*), pp. 5315–5320, (1998).

Thompson, C.B., "Apoptosin in the Pathogenesis and Treatment of Disease", *Science, 267*, pp. 1456–1462, (1995).

* cited by examiner

METHOD FOR PREDICTING TUMOR RECURRENCE

BACKGROUND OF THE INVENTION

Pediatric renal tumors account for about six percent of all childhood cancers in the United States. (1) The survival rate of pediatric patients with kidney tumors varies according to the respective pathology. Wilms' tumor has a good prognosis, with about an 80% cure rate; Clear Cell Sarcoma (CCS) of the kidney has a fair prognosis with about a 60% cure rate; whereas Rhabdoid tumors (RTK) of the kidney has a poor prognosis, with a cure rate of only about 10%. Despite this association, it is not uncommon to find that the behavior of a specific tumor is disparate with its pathologic diagnosis. Unfortunately, there are no recognized biologic markers (except for clinical stage and tumor type) for predicting prognosis or for guiding treatment, follow-up and counseling of pediatric patients with renal tumors.

Apoptosis, or programmed cell death, is the process by which activated cells undergo a suicide program that results in individual cell death. (2) It is a highly orchestrated process where cells die in a regulated fashion. Aberration in the process of apoptosis may contribute to the pathogenesis of certain tumors. (3) It has been shown that pro-apoptotic receptors were expressed at greater levels in Wilms' tumors of good prognosis, compared to CCS or RTK. (4) Surprisingly, no association was found with anti-apoptotic factors like Bcl-2 or Bcl-$X_L$ and prognosis.

An excess of apoptosis inhibitors could protect dividing cells from dying, and thus contribute to tumorigenicity. A related family of Inhibitors of Apoptosis proteins (IAP) has been described in many species and these proteins block apoptosis by direct inhibition of downstream effector caspases in the pathway of cell death. (5,6) A novel member of the IAP gene family designated Survivin was recently described and shown to be associated with tumors of poor prognosis. (7–10) Survivin is selectively expressed in tissues during development but not in terminally differentiated mature tissue and is also expressed in several pediatric renal tumors tested. (11) Survivin appears to block default induction of apoptosis during mitosis, and when over expressed in cancer cells, Survivin may permit aberrant proliferation through mitosis.

Currently, for many types of tumors there are no available markers specific for the tumor type. Thus, for these tumor types, treatment cannot be specifically guided nor can prognosis be predicted. Therefore, there is an ongoing need for methods and kits to predict recurrent tumor growth, in particular solid tumors and hematologic cancers. Such an indicator would be helpful not only for guiding the patient as to outcome, but also for selecting treatment groups as well as follow-up during treatment of disease.

SUMMARY OF THE INVENTION

The present invention provides a diagnostic method for predicting the recurrence of a tumor or cancer in a mammal by contacting RNA from a mammalian physiological sample suspected of being tumorigenic or cancerous with a Survivin-specific oligonucleotide comprising a first label, and a pro-apoptosis factor (PAF)-specific oligonucleotide comprising a second label under conditions effective to hybridize the RNA to the oligonucleotides so as to yield a first population of RNA labeled with the Survivin-specific oligonucleotide and a second population of RNA labeled with the PAF-specific oligonucleotide; quantifying the first and second populations of labeled RNA to determine an amount of Survivin RNA and an amount of PAF RNA present in the sample; and calculating the ratio of the amount of Survivin RNA and the amount of PAF RNA; wherein a Survivin:PAF ratio of more than about 1.5 is predictive that the tumor will recur. The Survivin:PAF ratio may be more than about 1.6, or even more than about 2.0. The PAF may be Fas, BID, p53, DR4 (TRAIL-R1), DR5 (TRAIL-R2), or TNF-R. The physiological sample may be a tissue sample, such as a tissue-lysate protein sample. The tissue may be any solid tumor, encompassing childhood and adult tumors. Pediatric examples include Neuroblastoma, Pediatric renal tumors, Hepatoblastoma, Rhabdomysosarcoma and undifferentiated sarcomas as well as germ cell and endocrine tumors. Adult examples would include tumors of the nervous system, gastrointestinal and urogenital tract, as well as all types of sarcomas. Alternatively, the physiological sample may be a fluid, such as whole blood or blood serum.

The present invention also provides a diagnostic method for predicting the recurrence of a tumor or cancer in a mammal by contacting a mammalian tissue sample suspected of being tumorigenic or cancerous with a Survivin-specific ligand comprising a first label, and a pro-apoptosis factor (PAF)-specific ligand comprising a second label under conditions effective to hybridize protein present in the tissue sample to the ligands so as to yield a first population of protein hybridized to the Survivin-specific ligand and a second population of protein hybridized to the PAF-specific ligand; quantifying the first and second populations of labeled protein to determine an amount of Survivin and an amount of PAF present in the sample; and calculating the ratio of the amount of Survivin and the amount of PAF; wherein a Survivin:PAF ratio of more than about 1.5 is predictive that the tumor will recur. The Survivin:PAF ratio may be more than about 1.6, or even more than about 2.0. The PAF may be Fas, BID, p53, DR4 (TRAIL-R1), DR5 (TRAIL-R2), or TNF-R. The physiological sample may be a tissue sample, such as a tissue-lysate protein sample. The tissue may be any solid tumor, encompassing childhood and adult tumors. Pediatric examples include Neuroblastoma, Pediatric renal tumors, Hepatoblastoma, Rhabdomysosarcoma and undifferentiated sarcomas as well as germ cell and endocrine tumors. Adult examples would include tumors of the nervous system, gastrointestinal and urogenital tract, as well as all types of sarcomas. Alternatively, the physiological sample may be a fluid, such as whole blood or blood serum. The agent may be an antibody, in particular a population of polyclonal or monoclonal antibodies.

The present invention further provides a diagnostic kit for predicting recurrence of tumor or cancer in a mammal, containing packaging material, a Survivin-specific ligand, a PAF-specific ligand and instructions means directing the use of (a) and (b) in accord with the above described methods.

BRIEF DESCRIPTION OF THE FIGURES

WTI=Wilms' tumor stage I, RTK IIIP=Rhabdoid tumor stage III, CCS III and IV=Clear cell sarcoma stage III and IV.

DETAILED DESCRIPTION OF THE INVENTION

Apoptosis factors that induce or prevent cell death affect the survival of certain tumors. In a simplified apoptosis model, an abundance of factors preventing cell death, and/or a depletion of factors promoting cell death increase the probability of tumor survival.

Survivin is an inhibitor of apoptosis that is expressed in a cell cycle dependent manner. It is present in fetal tissue and in most adult tumors, but is absent in differentiated normal adult tissue. Survivin is expressed in multiple tumors and is associated with both unfavorable histology and higher stage of disease. (7–10) For example, Survivin is associate with neuroblastoma, bladder cancer and colorectal cancer. Survivin appears to block default induction of apoptosis during mitosis, and thus when over-expressed in cancer cells, Survivin may permit aberrant proliferation through mitosis. (13) It is a member of the Inhibitors of Apoptosis family and is the only anti-apoptotic factor described thus far that appears to be cell cycle dependent.

Survivin is expressed in the G2/M (mitosis) phase of the cell cycle and has binding affinity for tubulin, which is the monomeric constituent of microtubules. (13) Microtubules play a critical role in chromosome organization as part of the mitotic spindle array during mitosis. Via immunofluorescence studies and co-sedimentation experiments, Survivin was found to aggregate with assembled microtubules in a concentration dependent manner. (14) Although Survivin's anti-apoptosis effects appear to be dependent on microtubule binding, Survivin also binds to and inhibits caspase 3, a downstream protease in the apoptosis cascade. (15) Amongst other sites of action, caspase 3 cleaves proteins in the mitotic spindle, leading to disruption of the mitotic spindle and cell death. Survivin inhibits caspase 3 activity by binding in a concentration dependent manner and thus inhibits several pathways of cell death that depend on caspase 3 as a downstream effector. Inhibition of Survivin expression by anti-sense oligonucleotides or a dominant-negative mutant enabled caspase 3 to cleave the mitotic spindle array, inducing apoptosis. (14)

An additional effect observed following Survivin inhibition is centrosome dysregulation and polyploidy defects (anywhere from 6N to 12N). (14) The presence and action of the p21 protein may explain this effect p21 is an inhibitor of the cell cycle control protein cyclin-dependent kinase (CDK), which is responsible for promoting centrosome duplication. Survivin inhibition resulted in the cleavage of both microtubules and p21 by caspase 3. In the context of this inhibitory effect, the uninhibited CDK protein can then promote irregular centrosome duplication resulting in polyploidy and multinucleated cells. These observed functions suggest that Survivin plays an important role in cell proliferation and thus its expression in tumors of higher grade and worse prognosis would compliment its proposed function as an anti-apoptotic protein in tumor cell division.

Unlike Survivin, Fas is a pro-apoptotic factor and is a member of the TNF related family of "death receptors". (16) Expression of Fas by pediatric renal tumors of good prognosis implicate tumor cell destruction by immune effector cells. (4) Relating prognosis to expression of pro-apoptotic receptors is an appealing concept, because both immune surveillance cytotoxic T-cells and Natural Killer cells use this receptor pathway during target cell destruction. Survivin was shown to inhibit apoptosis induced by several ligands of the TNF related family of receptors; thus enhancing cell survival and preventing cell death. (15,11) Current literature suggests that the functions of Survivin and Fas are dependent on one another (5), but it is also possible that these two factors may act independently in regulating apoptosis pathways. Although the present inventors have shown that Survivin inhibits apoptosis induced by TNF and TRAIL (TNF related apoptosis inducing ligand) (11), surprisingly, the inventors found that Fas mediated cell death was not inhibited by Survivin.

The present study shows that abundant expression of an anti-apoptotic factor and the absence of a pro-apoptotic factor appear to be associated with recurrence of tumor. For example, Survivin expression was compared to that of a pro-apoptotic factor (PAF), such as Fas, BID and p53, and computed as a Survivin:PAF ratio. It was found, that Survivin was more frequently expressed in primary tumors that went on to recur. Furthermore, it was found that the ratio of expression between these two apoptotic factors in primary tissue specimens was a sensitive and specific test for predicting recurrence of tumor. It is of interest to note that other anti-apoptotic factors including those of the Bcl-2 family were not associated with tumor outcome. Of the twenty-five apoptosis regulating factors that the present inventors have screened by RNase protection assay (RPA) to date, only Survivin and several of the TNF related receptors (i.e. Fas, 5 and TNF-R) appear to be differentially expressed in pediatric renal tumors. (11)

Using the molecular markers described in this study and calculating the Survivin:Fas ratio may help predict the clinical course and eventual outcome of pediatric patients with renal tumors. Previously, the main predictors of outcome for these patients were the pathologic type and clinical stage of the tumor. Although these observations were extremely important, they did not consider the biology of the tumor. Thus the behavior of a specific tumor type may be disparate with its pathologic diagnosis (e.g. Wilms' tumor that recurs or RTK that goes into remission). The ability to predict recurrence of disease can guide the treatment, follow-up and counseling of patients with tumors.

The ratio between Survivin and Fas can be calculated for any solid tumor or hematologic cancer, even those that do not have known molecular markers that are indicative of recurrence or prognosis. The discovery of the predictive value of this molecular ratio is novel and overcomes the previous problem of not being able to determine the prognosis of many tumors and cancers. Although the concept of an excess of pro-apoptotic (death) factors decreasing tumorigenicity and an excess of anti-apoptotic (survival) factors enhancing tumorigenicity is not new, the combination of Survivin and PAF values into a single ratio has not been previously reported. Thus the present methods and kits that specifically evaluate the Survivin:PAF ratio are useful for many tumor types. The PAF may be Fas, BID, p53, DR4 (TRAIL-R1), DR5 (TRAIL-R2), or TNF-R. The Survivin:PAF ratios will vary depending on the PAF used, but an appropriate predictive ratio will be easily ascertainable by one having skill in the art.

Figure 1:
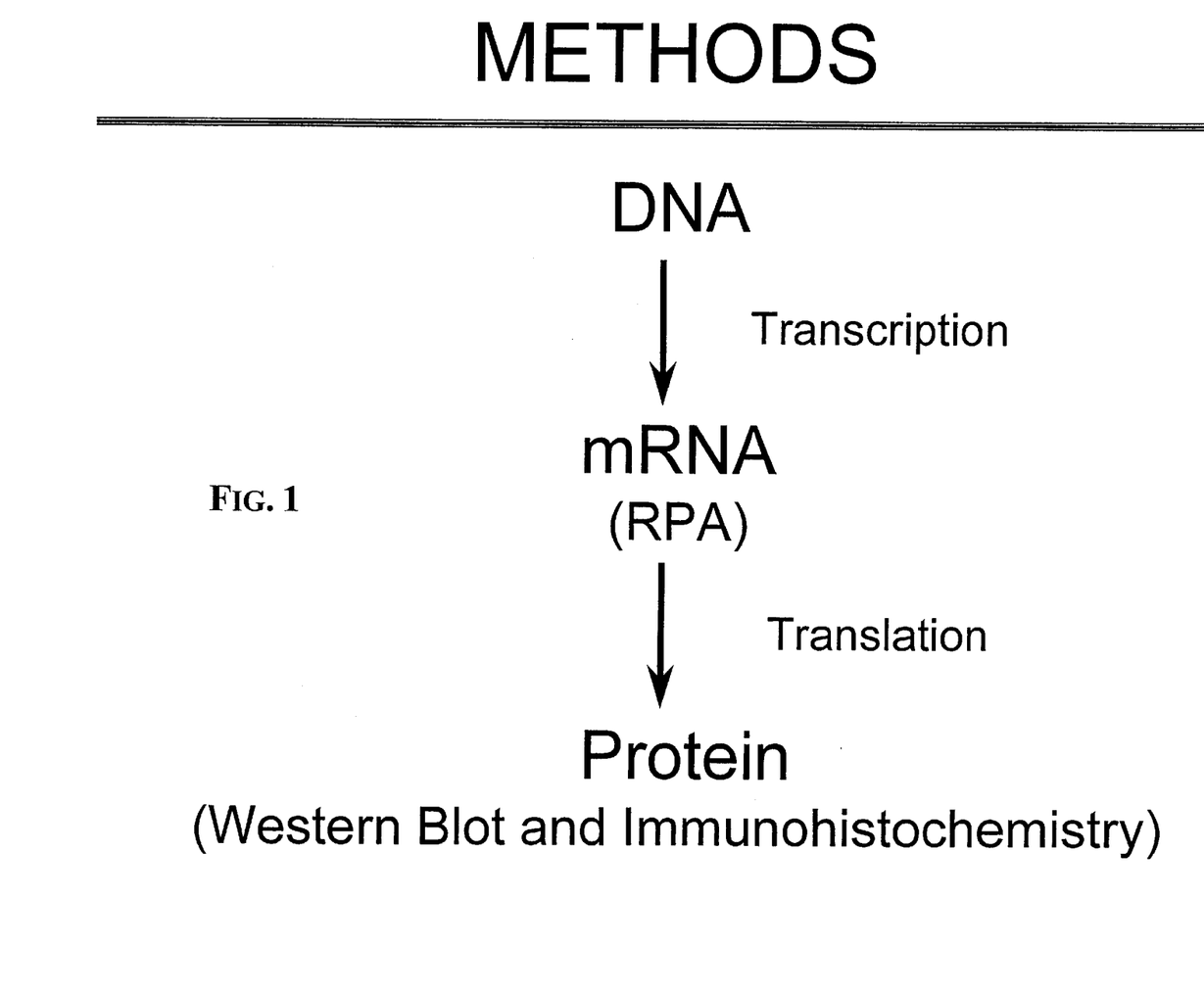
FIG. 1: Methods of determining quantity of pro- and anti-apoptotic factors present in a tissue sample.

In particular, the method of the present invention may be practiced as follows. A biopsy of the tumor, or cancerous tissue or cells, is obtained. The biopsy may be from a solid tumor. Pediatric examples include Neuroblastoma, Pediatric renal tumors, Hepatoblastoma, Rhabdomysosarcoma and undifferentiated sarcomas as well as germ cell and endocrine tumors. Adult examples include tumors of the nervous system, gastrointestinal and urogenital tract, as well as all types of sarcomas, and hematologic cancers. The amount of apoptotic inhibitor and pro-apoptotic factor is then quantified either directly or indirectly. (FIG. 1.) For example, one way to quantify these factors is to measure the factor by quantifying the amount of RNA present using an RNase Protection Assay (RPA). Briefly, RNA is isolated from the tissues of interest, and an anti-sense RNA probe is hybridized in excess to the target RNA in solution. Free probe and non-hybridized single stranded RNA were digested with RNases. Labeled anti-sense RNA is transcribed incorporating a labeled nucleotide, such as an [$\alpha$-$^{32}$P]UTP. Total RNA is extracted from tissue. The amount of labeled mRNA was then quantified. Other methods to quantify the apoptotic inhibitor and pro-apoptotic factor of interest include by Western blot or by immunohistochemical staining. Other RNA and protein detection methods are well-known to those with skill in the art.

Thus, the present inventors have discovered that Survivin is more abundant in tumors that recur, and that PAFs, such as Fas are more abundant in tumors that are cured. The inventors have found that the Survivin:Fas ratio is a powerful predictor of recurrent disease, and assists in guiding treatment, counseling and follow-up therapeutic strategies with patients with tumors. In particular, a Survivin:Fas ratio of greater than about 1.5, or greater than about 1.6, or even at greater than 2.0, is a highly sensitive and specific predictor of tumor recurrence.

Detection Labels

The labels used in the assays of invention can be primary labels (where the label comprises an element that is detected directly) or secondary labels (where the detected label binds to a primary label, e.g., as is common in immunological labeling). An introduction to labels (also called "tags"), tagging or labeling procedures, and detection of labels is found in Polak and Van Noorden (1997) *Introduction to Immunocytochemistry*, second edition, Springer Verlag, N.Y. and in Haugland (1996) *Handbook of Fluorescent Probes and Research Chemicals*, a combined handbook and catalogue Published by Molecular Probes, Inc., Eugene, OR. Primary and secondary labels can include undetected elements as well as detected elements. Useful primary and secondary labels in the present invention can include spectral labels such as fluorescent dyes (e.g., fluorescein and derivatives such as fluorescein isothiocyanate (FITC) and Oregon Green™, rhodamine and derivatives (e.g., Texas red, tetramethylrhodamine isothiocyanate (TRITC), etc.), digoxigenin, biotin, phycoerythrin, AMCA, CyDyeS™, and the like), radiolabels (e.g, $^3$H, $^{125}$I, $^{35}$S, $^{14}$C, $^{32}$P, $^{33}$P), enzymes (e.g., horse-radish peroxidase, alkaline phosphatase) spectral calorimetric labels such as colloidal gold or colored glass or plastic (e.g. polystyrene, polypropylene, latex) beads. The label may be coupled directly or indirectly to a component of the detection assay (e.g., the labeled nucleic acid) according to methods well known in the art. As indicated above, a wide variety of labels may be used, with the choice of label depending on sensitivity required, ease of conjugation with the compound, stability requirements, available instrumentation, and disposal provisions. In general, a detector that monitors a probe-substrate nucleic acid hybridization is adapted to the particular label that is used. Typical detectors include spectrophotometers, phototubes and photodiodes, microscopes, scintillation counters, cameras, film and the like, as well as combinations thereof. Examples of suitable detectors are widely available from a variety of commercial sources known to persons of skill. Commonly, an optical image of a substrate comprising bound labeled nucleic acids is digitized for subsequent computer analysis.

Preferred labels include those that use (1) chemiluminescence (using Horseradish Peroxidase and/or Alkaline Phosphatase with substrates that produce photons as breakdown products) with kits being available, e.g., from Molecular Probes, Amersham, Boehringer-Mannheim, and Life Technologies/Gibco BRL; (2) color production (using both Horseradish Peroxidase and/or Alkaline Phosphatase with substrates that produce a colored precipitate) (kits available from life Technologies/Gibco BRL, and Boehringer-Mannheim); (3) hemifluorescence using, e.g., Alkaline Phosphatase and the substrate AttoPhos (Amersham) or other substrates that produce fluorescent products, (4) Fluorescence (e.g., using Cy-5 (Amersham), fluorescein, and other fluorescent labels); (5) radioactivity using kinase enzymes or other end-labeling approaches, nick translation, random priming, or PCR to incorporate radioactive molecules into the labeled nucleic acid. Other methods for labeling and detection will be readily apparent to one skilled in the art.

Fluorescent labels are highly preferred labels, having the advantage of requiring fewer precautions in handling, and being amendable to high-throughput visualization techniques (optical analysis including digitization of the image for analysis in an integrated system comprising a computer). Preferred labels are typically characterized by one or more of the following: high sensitivity, high stability, low background, low environmental sensitivity and high specificity in labeling. Fluorescent moieties, which are incorporated into the labels of the invention, are generally are known, including Texas red, dixogenin, biotin, 1- and 2-aminonaphthalene, p,p'-diaminostilbenes, pyrenes, quaternary phenanthridine salts, 9-aminoacridines, p,p'-diaminobenzophenone imines, anthracenes, oxacarbocyanine, merocyanine, 3-aminoequilenin, perylene, bis-benzoxazole, bis-p-oxazolyl benzene, 1,2-benzophenazin, retinol, bis-3-aminopyridinium salts, hellebrigenin, tetracycline, sterophenol, benzimidazolylphenylamine, 2-oxo-3-chromen, indole, xanthen, 7-hydroxycoumarin, phenoxazine, calicylate, strophanthidin, porphyrins, triarylmethanes, flavin and many others. Many fluorescent labels are commercially available from the SIGMA Chemical Company (Saint Louis, Mo.), Molecular Probes, R&D systems (Minneapolis, Minn.), Pharmacia LKB Biotechnology (Piscataway, N.J.), CLONTECH Laboratories, Inc. (Palo Alto, Calif.), Chem Genes Corp., Aldrich Chemical Company (Milwaukee, Wis.), Glen Research, Inc., GIBCO BRL Life Technologies, Inc. (Gaithersberg, Md.), Fluka ChemicaBiochemika Analytika (Fluka Chemie AG, Buchs, Switzerland), and Applied Biosystems (Foster City, Calif.), as well as many other commercial sources known to one of skill.

Means of detecting and quantifying labels are well known to those of skill in the art. Thus, for example, where the label is a radioactive label, means for detection include a scintillation counter or photographic film as in autoradiography. Where the label is optically detectable, typical detectors include microscopes, cameras, phototubes and photodiodes and many other detection systems that are widely available.

Definitions

As used herein, the term "RNA probe" means a nucleic acid sequence that has at least about 80%, more preferably at least about 90%, and more preferably at least about 95%, contiguous sequence identity or homology to the RNA sequence encoding the apoptotic inhibitor and pro-apoptotic factor of interest. A probe (or oligonucleotide or primer) of the invention has at least about 7–50, preferably at least about 10–40, and more preferably at least about 15–35, nucleotides. Preferably, the oligonucleotide primers of the invention comprise at least about 7 nucleotides at the 3' of the oligonucleotide primer which have at least about 80%, more preferably at least about 85%, and more preferably at least about 90%, contiguous identity to the apoptotic inhibitor and pro-apoptotic factor of interest.

As used herein, the term "Survivin sequence" (or other apoptotic inhibitor or pro-apoptotic factor of interest) includes the prepro, pro and mature forms of the apoptotic inhibitor and pro-apoptotic factor of interest, as well as variants and/or subunits of those polypeptides. Thus, for example, a mature Survivin polypeptide, as well as variant Survivin polypeptides which share at least 90% homology with the known Survivin sequence, are within the scope of the term "Survivin polypeptide." Preferably, the Survivin or PAF polypeptides, variant polypeptides, or subunits thereof, are biologically active. The biological activity of a Survivin or PAF polypeptide of the invention can be detected by methods well known to the art including, but not limited to, the ability to react with antibodies specific for Survivin or PAF polypeptides. Thus, the Survivin or PAF polypeptides of the invention possess antigenic function in common with the mature Survivin or PAF molecule in that the polypeptides are also definable by antibodies which bind specifically to Survivin or PAF. Preferably, the antibodies react with antigenic sites or epitopes that are also present on the mature Survivin or PAF molecule.

"Isolated Survivin (or PAF) nucleic acid" is RNA or DNA containing greater than 7, preferably 15, and more preferably 20 or more, sequential nucleotide bases that are complementary to the native Survivin RNA or PAF RNA, or hybridizes to the RNA and remains stably bound under stringent conditions. Preferably, the isolated nucleic acid encodes a biologically active Survivin or PAF polypeptide, a variant thereof, or a subunit thereof.

Thus, the RNA is isolated in that it is free from at least one contaminating nucleic acid with which it is normally associated in the natural source of the nucleic acid and is preferably substantially free of any other mammalian RNA or DNA. The phrase "free from at least one contaminating nucleic acid with which it is normally associated" includes the case where the nucleic acid is reintroduced into the source or cell from which it was derived but is in a different chromosomal location or is otherwise flanked by nucleic acid sequences not normally found in the source or cell. An example of isolated Survivin or PAF nucleic acid is RNA that encodes a biologically active Survivin or PAF polypeptide sharing at least 90% sequence identity with the known Survivin or PAF sequence, as described above. The term "isolated, purified" as used with respect to a Survivin or PAF polypeptide is defined in terms of methodologies well known to the art, e.g., see U.S. Pat. No. 6,103,237.

"Northern analysis" or "Northern blotting" is a method used to identify RNA sequences that hybridize to a known probe such as an oligonucleotide, DNA fragment, cDNA or fragment thereof, or RNA fragment. The probe is labeled with a radioisotope such as $^{32}P$, by biotinylation or with an enzyme. The RNA to be analyzed can be usually electrophoretically separated on an agarose or polyacrylamide gel, transferred to nitrocellulose, nylon, or other suitable membrane, and hybridized with the probe, using standard techniques well known in the art.

"Stringent conditions" are those that (1) employ low ionic strength and high temperature for washing, for example, 0.015 M NaCl/0.0015 M sodium citrate (SSC); 0.1% sodium lauryl sulfate (SDS) at 50° C., or (2) employ a denaturing agent such as formamide during hybridization, e.g., 50% formamide with 0.1% bovine serum albumin/0.1% Ficoll/0.1% polyvinylpyrrolidone/50 mM sodium phosphate buffer at pH 6.5 with 750 mM NaCl, 75 mM sodium citrate at 42° C. Another example is use of 50% formamide, 5×SSC (0.75 M NaCl, 0.075 M sodium citrate), 50 mM sodium phosphate (pH 6.8), 0.1% sodium pyrophosphate, 5×Denhardt's solution, sonicated salmon sperm DNA (50 $\mu$g/ml), 0.1% SDS, and 10% dextran sulfate at 42° C., with washes at 42° C. in 0.2×SSC and 0.1% SDS. Other examples of stringent conditions are well known in the art.

The invention will be further described by reference to the following detailed examples.

EXAMPLE 1

The Survivin:Fas Ratio in Pediatric Renal Tumors

Materials and Methods

Tissue specimens: Thirty two frozen tissue specimens were obtained from pediatric patients with renal tumors prior to chemotherapy at the University of Iowa Hospitals and Clinics and from the National Wilms' Tumor Study group (NWTSG) tissue bank. Eleven normal kidney and 21 tumor specimens were assayed for expression of multiple mRNA species including Survivin and Fas. Normal kidney specimens were obtained from tissue adjacent to the resected tumors. The following pediatric renal tumors were assayed: Wilms' tumor (WT): Stage I (n=1), II (n=4), III (n=3), IV (n=1); Mesoblastic Nephroma (n=3); Clear cell sarcoma (CCS) stage II (n=2), III (n=1), IV (n=1); and Rhabdoid tumor of the kidney (RTK) stage II (n=2), III (n=1), IV (n=2). As a control, tissue from normal kidney (NK) was also tested (n=11).

RNase Protection Assay (RPA): The RiboQuant™ Multiprobe protection assay system (PharMingen, San Diego, Calif.) is a highly sensitive and specific method for simultaneous detection and quantification of multiple mRNA species. Human apoptosis template probe sets are available, and we have customized a template (Custom human template set; PharMingen, San Diego, Calif.) to detect expression of XIAP, Survivin, Fas, DCR1, DR3, DR5, DR4, Bax, TNF-R1, L32 and GAPDH. These mRNA species were selected from our previous studies, in which we examined 23 different mRNA's in pediatric renal tumors. (11) The selected group includes those mRNA species that appeared to be differentially expressed in these tumors.

After isolating RNA from the tissues of interest, the anti-sense RNA probe was hybridized in excess to target RNA in solution. Free probe and non-hybridized single stranded RNA were digested with RNases. $^{32}P$-labeled antisense RNA was transcribed using T7 RNA polymerase (PharMingen) and [$\alpha$-$^{32}P$]UTP (Amersham LIFE SCIENCE, England). Total RNA was extracted from tissue using TRIZOL(GIBCO LIFE TECHNOLOGIES, Md.).

Fourteen to 16 μl g of total RNA was hybridized with the $^{32}$P-labeled RNA probes which were transcribed from the customized multiprobes (DNA templates) at 56° C. overnight, followed by digestion with a 1:417 dilution of RNase "cocktail" (RNase A:T1 mixture; PharMingen) for 45 minutes at 30° C. Single stranded and unhybridized excess mRNA was digested by the RNase "cocktail". The protected-double-stranded RNA pellets were dried and re-suspended in 5 μl of 1×loading buffer (PharMingen), and electrophoretically resolved on 5% polyacrylamide-8 M urea gel. The polyacrylamide-urea gel was dried on blotting paper for 1 hour at 80° C. The labeled probes were then quantified by autoradiography by exposing the blotting paper to BIO MAX FILM (Kodak, N.Y.) with an intensifying screen (Kodak) for 20 hours at −80° C.

Radio-analytic imaging: For comparative analysis, we quantified mRNA species expression as a percentage of the ribosomal protein L32 mRNA expression. Radioactivity of each band in the sample was quantified, standardized and compared to L32 expression of that sample. Radioactivity of each template was quantified directly from the gel by a radio-analytic imaging system (AMBIS 4000, AMBIS Inc., San Diego, Calif.) equipped with AMBIS QuantProbe Software Version 3.0 for 1,000 min. Net counts were obtained from each template (band) including L32, and the radioactivity was expressed as a percent of the L32 activity.

Western blot for protein expression: The standard technique of Western Blot (WB) was performed. Briefly, tissue lysate proteins were isolated by solubilizing cells with RIPA buffer and protease inhibitors. The protein content was equilibrated between samples by using the Lowry protein assay to quantify protein isolated. (12) Isolated proteins (120 ug) were separated by SDS-PAGE (12%) under non-reducing conditions after placing in Laemmli buffer. Subsequently, proteins were electrophoretically transferred to a nitrocellulose membrane at 210 mAmps for 4 hours. Membranes were subsequently blocked in TBS with 0.1% Tween 20 plus 5% skim milk overnight at 4° C. Following washes, membranes were then incubated with mouse monoclonal antibody to Survivin (8E2 provided by Dr Altieri. Yale University) (2 ug/ml). Again after several washes, membranes were incubated with a 1:2500 dilution of HRP-labeled goat anti-mouse IgG secondary antibody (SIGMA, MO) at room temperature for I hour. Bands were viewed by a chemiluminescence reaction using the chemiluminescence system (ECL; Amersham, Arlington Heights, Ill.).

Immunohistochemical staining (IHC): Five micrometer tumor sections cut on a microtome were mounted on microscope slides and air dried for staining. After fixation in acetone, endogenous peroxidase was quenched with 0.3% H2O2 in methanol at room temp. Nonspecific binding sites were blocked with 1.5% normal blocking serum in PBS. Primary rabbit polyclonal antibody to Survivin (2 ug/ml) (provided by Dr Altieri, Yale University) diluted 1:5 was added overnight at 4° C. Primary antibody was visualized with biotinylated secondary antibody (goat anti-rabbit) (SIGMA, MO) and horseradish peroxidase-conjugated avidin (ABC kit, Vector Laboratories). Samples were color developed with 3.3'-Diaminobenzidine (DAB) (SIGMA, MO) and counterstained with hematoxylin.

Data analysis: Survivin and Fas expression as well as Survivin:Fas ratios were determined and compared among three groups of tissue specimens using the Kriskall-Wallis non-parametric test. These groups included: normal kidney, tumors that went on to recur and tumors that did not recur. Since we found a significant association between a high Survivin:Fas ratio and recurrence of tumor, we used the Survivin:Fas ratio as a predictor of recurrent tumor. Sensitivity, specificity, positive and negative predictive values of this ratio were computed. The median, mean and standard deviations are presented.

Results

Outcomes: We examined 32 tissue specimens of which 10 were primary tumors that went on to recur, 11 were primary tumors that did not recur and 11 were specimens of normal kidney sampled adjacent to tumors. The group of recurrent tumors included: WT (Stage I n=1, Stage III n=2); CCS (Stage II n=1, stage III n=1 and stage IV n=1) and RTK (Stage II n=1, stage III n=1 and stage IV n=2). The group of non-recurrent tumors included: WT (Stage II n=4, Stage III n=1 stage IV n=1); MN (n=3), CCS (Stage II n=1), and RTK (Stage II n=1).

Figure 2:
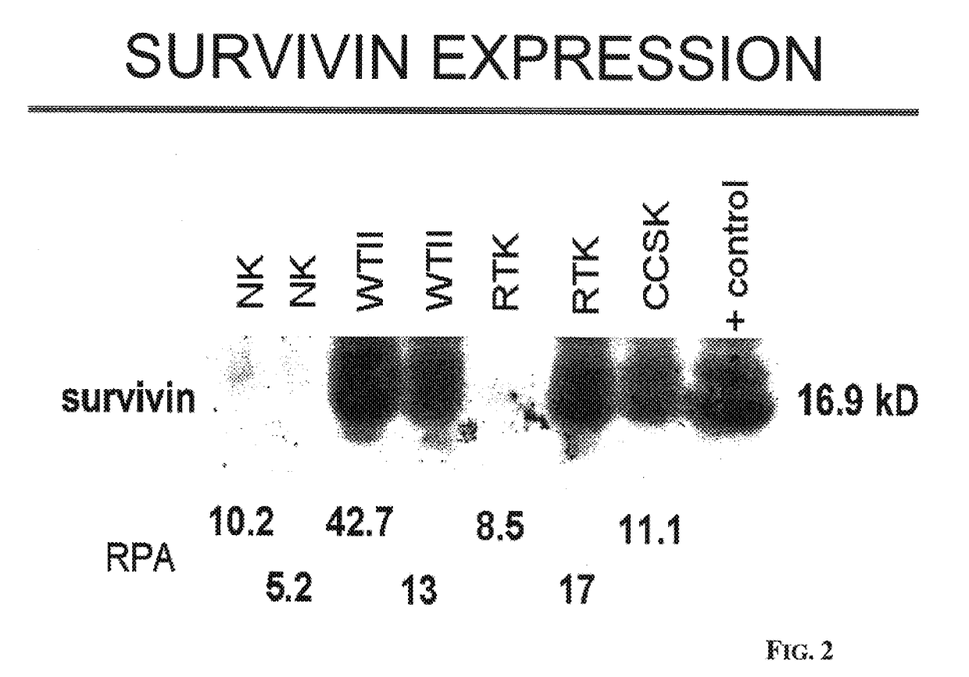
FIG. 2: Western blot analysis of several pediatric renal tumors and corresponding RPA values. NK=Normal Kidney; WTII=Wilms' tumor stage II; RTK=Rhabdoid tumor of the kidney; CCS=Clear cell sarcoma of the kidney. RPA= RNase protection assay calculated as percent of L32 expression.
Figure 3:
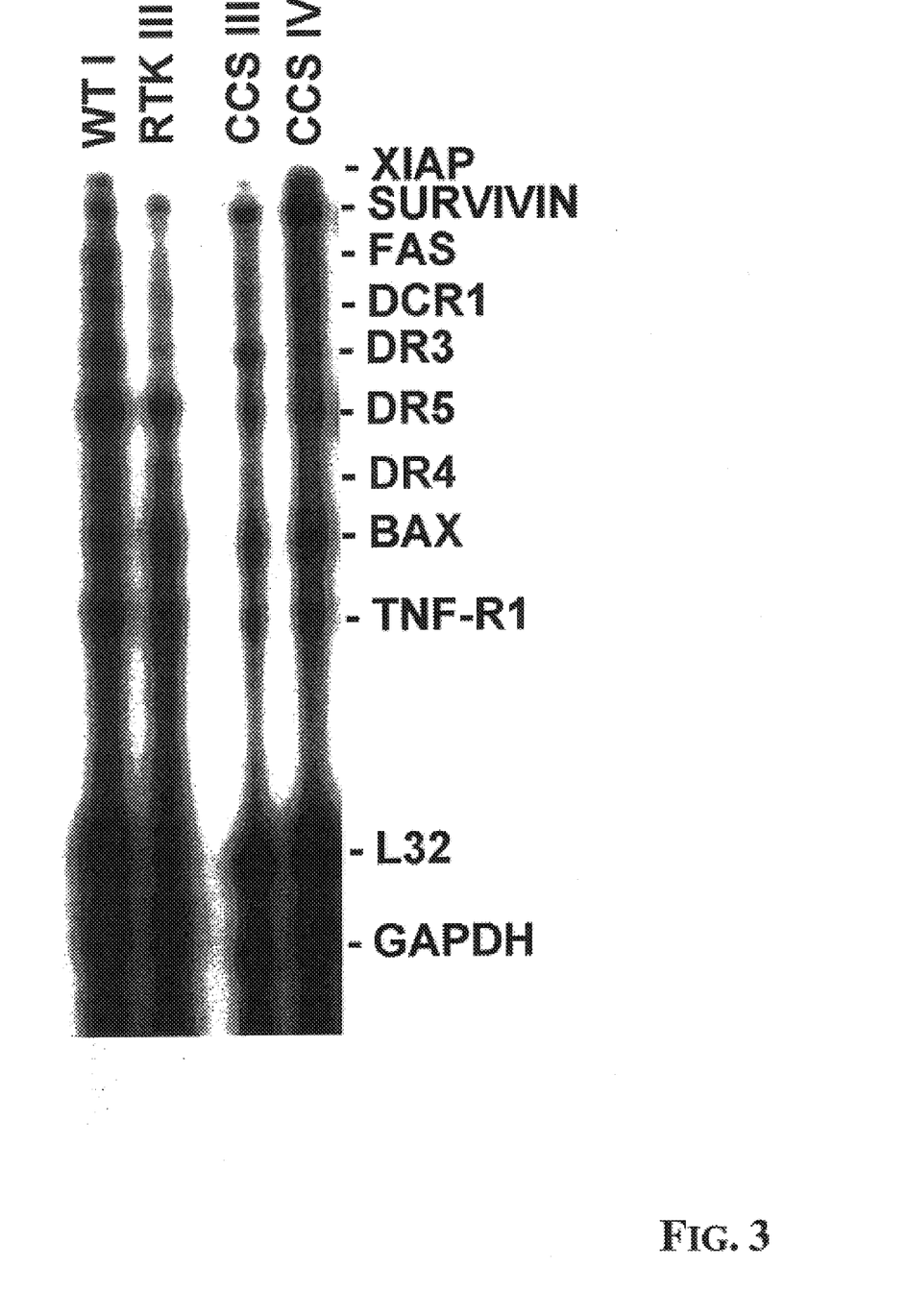
FIG. 3: Autoradiographic plate of RNase protection assay (RPA) showing bands marking the various mRNA species detected in four examples of pediatric renal tumors studied.

RNase protection assay (RPA) and Western blot analysis: We compared quantification by RPA to Western blot analysis and found that a Survivin mRNA level of 10 percent or less was not detected by Western blot. (FIG. 2.) Thus, for gross analysis of tissue specimens, we assumed that Survivin expressed as 10% of L32 or less (detected by RPA) was negative for Survivin expression. This observation held true for our limited immuno-histochemical survey as well. Survivin was expressed in multiple renal tumors of various stage and type, but was not present in normal Kidney. (FIGS. 2 and 3.) Overall, 50% (5/10) of tumors that went on to recur expressed Survivin while Survivin was present in only 18 percent (2/11) of tumors that failed to recur. Conversely, Fas was present in 45% (5/11) of tumors that were cured and was only present in 20% (2/10) of tumors that went on to recur. Fas was also present in 36% of normal Kidney specimens. (Table 1).

TABLE 1

| Pediatric Renal Tumors | | |
|---|---|---|
| | Survivin | Fas |
| No recurrence: | | |
| Tumor WT, MN, CCS, RTK | 2/11 (18%) | 5/11 (45%) |
| Recurrence: | | |
| Tumor WT, CCS, RTK | 5/10 (50%) | 2/10 (20%) |
| Normal Kidney: | 0/11 (0%) | 4/11 (36%) |

Table 1 indicates the presence of Survivin and Fas in primary pediatric renal tumors that failed to recur (No recurrence), in tumors that went on to recur (Recurrence), and in normal kidney (NK) specimens. Presence was determined as greater than 10% expression of L32 by RPA and selectively confirmed with western blot and immunohistochemistry.

Figure 4:
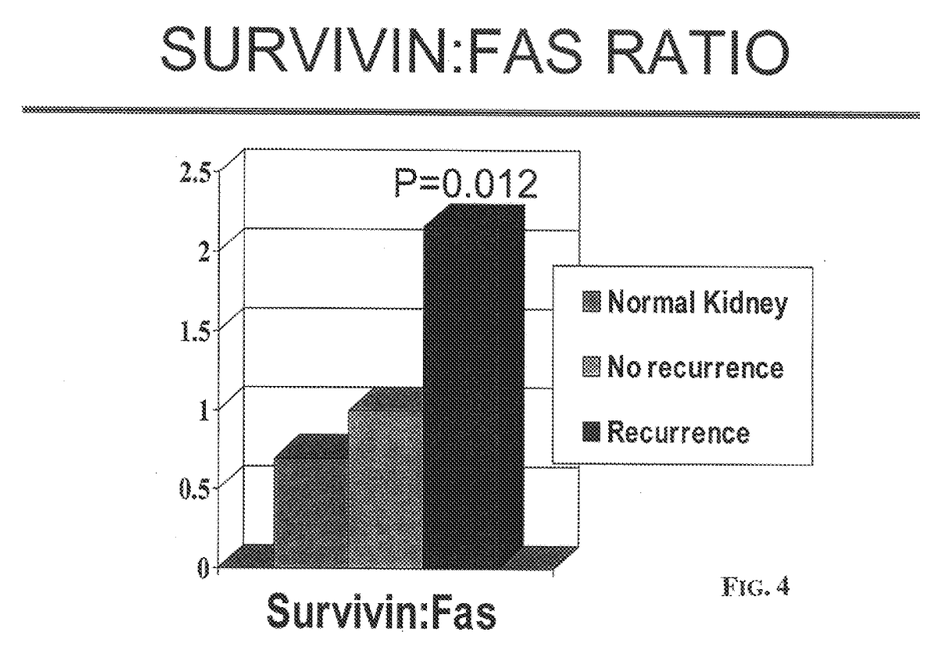
FIG. 4: Comparative chart for the Survivin:Fas ration calculated from RPA values for normal kidney, non-recurrent tumors, and recurrent tumors.

The Survivin:Fas ratio was calculated from RPA values and this ratio of mRNA expression was significantly greater in the group of tumors that went on to recur than in non-recurrent tumors (p=0.012) or normal Kidney (p=0.004). There was no difference in the ratio between normal Kidney and non-recurrent tumor (p=1.0) The median Survivin:Fas ratio in the recurrent group was 1.99 (mean 2.16±1.4). The median Survivin:Fas ratio in the non-recurrent disease group was 0.56 (mean 1.0±1.07). Seven of 10 tumors that went on to recur had a Survivin:Fas ratio of 1.6 or greater, while none of the 11 tumors that were cured had a ratio of 1.6 or greater. Using a Survivin:Fas ratio of 1.6 as a cut off, the sensitivity of this test was 60 percent (CI 26.2%, 87.8%) with a specificity of 90.9 percent (CI 58.7%, 99.8%). The positive predictive value of this ratio was 85.7% (CI 42.1%, 99.6%) and the negative predictive value was 71.4% (CI 41.9%, 91.6%). (FIG. 4.)

Figure 5:
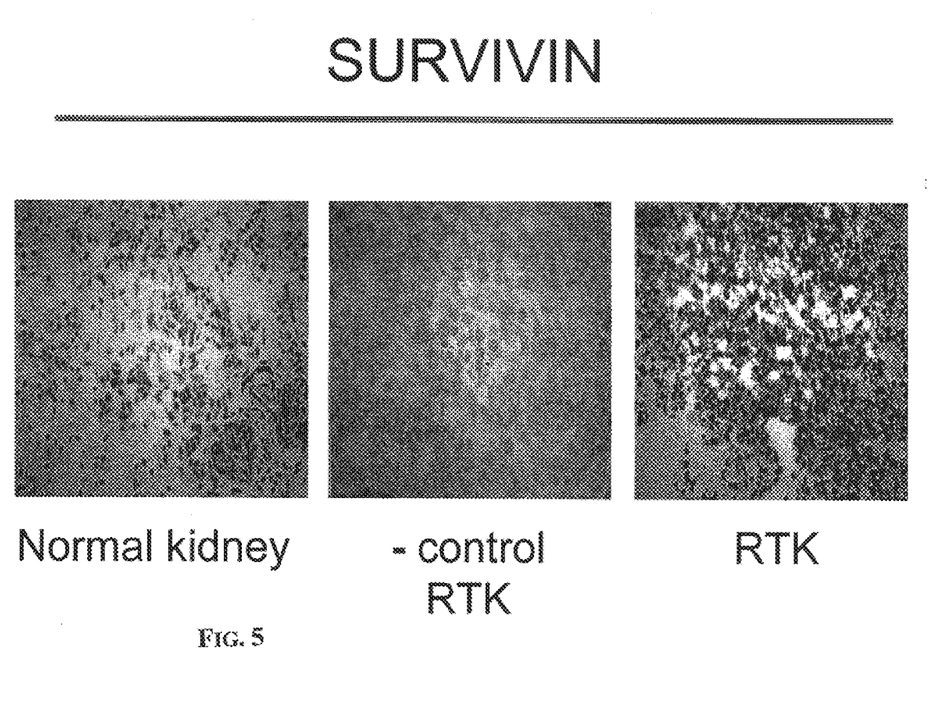
FIG. 5: Survivin immunoreactivity in examples of histologic specimens. A=Normal kidney, B=RTK Negative control (absent primary Ab) and C=RTK (Rhabdoid tumor of the kidney). Note positive (dark brown) intra-cellular Survivin staining in plate C and absence of Survivin staining in A and B.

Immunohistochemical Analysis: Strongly positive intracellular staining for Survivin was detected by immunohistochemistry in Survivin expressing tumors. Normal Kidney and several tumors failed to express Survivin, corroborating our observations of RPA and Western Blot analysis. (FIG. 5.)

EXAMPLE 2

The Survivin:Fas Ratio as a Predictor of Neuroblastoma Recurrence

Neuroblastoma (NB) is a malignant tumor of childhood that arises from primordial neural crest cells. This tumor accounts for 8–10% of all childhood cancers and for 15% of cancer related deaths in children. (17) NB is distinct in its ability to spontaneously regress, but more frequently presents as a markedly aggressive tumor with a high risk for recurrence.

Several clinical and biologic features of NB are used to predict the risk of recurrent disease. Many of the biologic markers used, potentially reflect the tumor's ability to differentiate, proliferate, or undergo apoptosis (programmed cell death). It is feasible that the balance between anti-apoptotic factors and pro-apoptotic factors within a tumor cell could impact the cell's survival.

Survivin is detected in many tumors but is not present in normal differentiated adult tissue. Survivin is expressed during cell proliferation in the G2/M phase of the cell cycle and its presence in tumors of patients with neuroblastoma, colorectal or gastric cancer portends a poor survival. (13) Conversely, the pro-apoptotic factor Fas is found to be more prevalent in pediatric renal tumors (4) and Neuroblastoma (18) of favorable prognosis. The ratio of Survivin to Fas (S:F ratio) can be used to predict the risk of recurrent disease in patients with neuroblastoma.

The expression of twenty-three different apoptotic mRNA species was quantified using RNase Protection Assay (Riboquant™, PharMingen, San Diego, Calif.). Twenty-six primary tumor specimens were evaluated from patients with ganglioneuroma (n=2), ganglioneuroblastoma (n=2), and neuroblastoma (n=22) from tumors of all clinical stages obtained at the time of diagnosis. Analysis of the results showed that the Survivin:Fas (S:F) ratio was significantly greater in tumors that went on to recur compared to those from patients that were cured. (Median S:F ratio: 3.30 vs. 0.89; p=0.0007 Wilcoxon rank-sum test). A cut-off ratio of 2.3 was also highly predictive of tumor recurrence, irrespective of clinical stage of disease (Area under ROC curve= 0.915) (Table 2).

TABLE 2

SURVIVIN:FAS RATIO AS A PREDICTOR OF NEUROBLASTOMA RECURRENCE

| Cut-off value S:F Ratio | Recurrent tumors | Non-recurrent Tumors |
| --- | --- | --- |
| <2.32 | 2 | 17 |
| ≧2.32 | 7 | 0 |

Sensitivity: 77.78% (CI: 40%–97.2%)
Specificity: 100% (CI: 83.8%–100%)
Positive Predictive Value: 100% (CI: 59%–100%)
Negative Predictive Value: 89.47% (CI: 61.9%–98.7%)

EXAMPLE 3

The Survivin:BID and Survivin:p53 Ratio in Tumors

A predictive ratio can be determined by measuring other pro-apoptotic factors in addition to Fas. For example, a Survivin:BID and Survivin:p53 can be computed and used to predict tumor cell aggression (i.e., growth rate, sensitivity to drugs and activation induced cell death).

Two recently examined tissue specimens from two patients with Neuroblastoma of good prognosis revealed low Survivin levels and notably high Bid levels. Ratios were 0.2 and 0.17. Similarly, in these two patients Survivin:p53 ratios were 0.18 and 0.16. Survivin:Fas ratios were 0.6 and 0.7 respectively.

Similarly in an evaluation of several human NB cell lines it was seen that the more Survivin was suppressed (drug effect), which correlated with a decreased Survivin:Bid or Survivin:p53 ratio, the more sensitive the cell lines became to either spontaneous or activation induced cell death.

EXAMPLE 4

Comparison of Surviving Bcl2 and TNF Related mRNA Species

Figure 6:
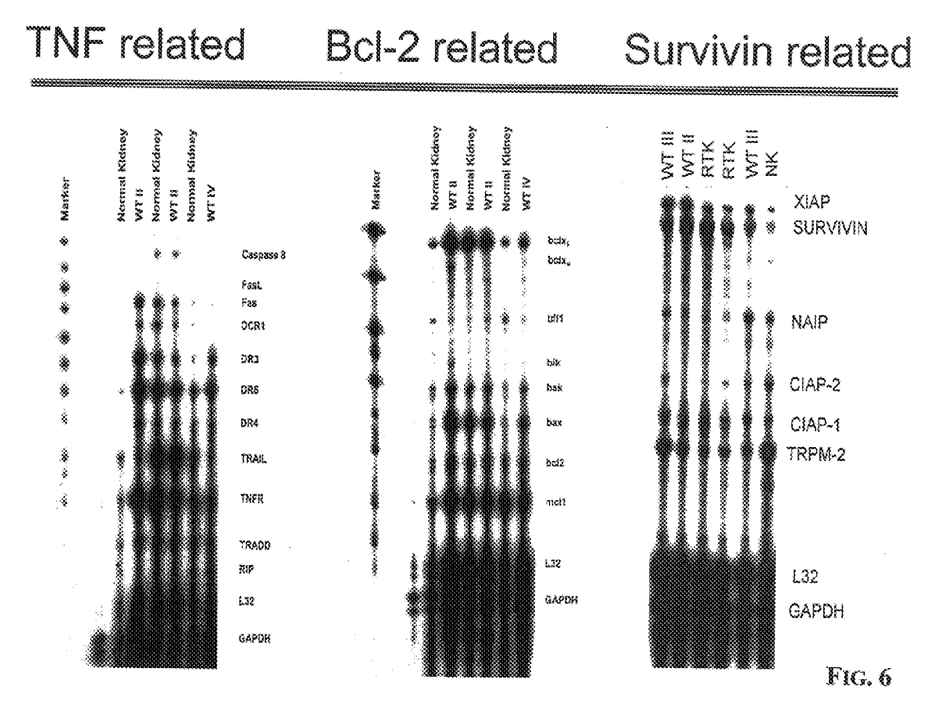
FIG. 6: The amount of TNF related, Bcl-2 related, and Survivin related RNA present in tumors as quantified radioanalytically (as measured as a percent of L32).

A comparative RNase Protection Assay (described in Example 1 above) was performed on six Survivin related (hApo-5c) mRNA species, eight Bcl-2 related (hApo-2) mRNA species, and eleven TNF related (hApo-3c) mRNA species. The amount of RNA present was quantified radio-analytically (as measured as a percent of L32). (FIG. 6.)

EXAMPLE 5

The Survivin:DR5 and Survivin:TNF-R Ratio in Tumors

Figure 7:
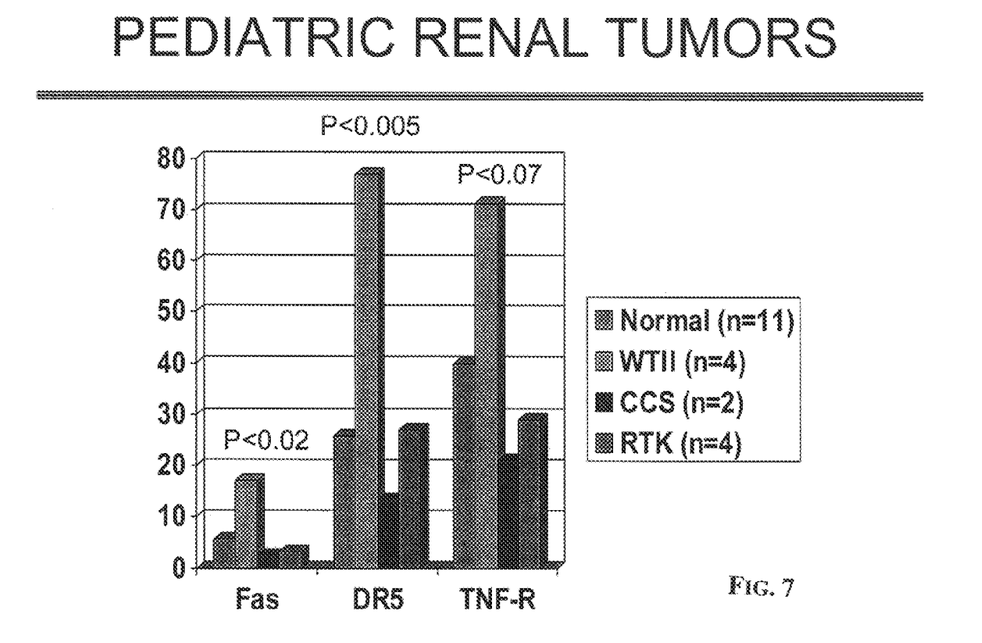
FIG. 7: Pediatric Renal Tumors. TNF related receptors (i.e. Fas, DR5 and TNF-R) that are differentially expressed in pediatric renal tumors.

Of the twenty-five apoptosis regulating factors that the present inventors have screened by RNase protection assay (RPA) to date, only Survivin and several of the TNF related receptors (i.e. Fas, DR5 and TNF-R) appear to be differentially expressed in pediatric renal tumors. (FIG. 7.) Therefore, the calculation of the Survivin:DR5 and Survivin TNF-R ratio could also assist with the prediction of tumor recurrence.

Several human renal cell carcinoma cell lines have been studied and it was found that the most resistant cell line has the highest Survivin:DR4 or Survivin DR5 ratio: 7860=2.96 and 2.4 respectively (resistant cell line). Sensitive cell lines include 769=0.54 and 0.17, A498=0.5 and 0.12; ACHN=1.0 and 0.34 respectively.

All patents and publications are incorporated by reference herein, as though individually incorporated by reference. Although preferred embodiments of the invention are described herein in detail, it will be understood by those skilled in the art that variations and modifications may be made thereto without departing from the spirit of the invention or the scope of the invention defined by the claims.

References

1. Breslow N, Olshan A, Beckwith J B, Green D M: Epidemiology of Wilms' tumor. Med Pediatr Oncol 21:172–181, 1993
2. Miller L, Marx J: Apoptosis. Science 281:1301, 1998
3. Thompson C B: Apoptosis in the pathogenesis and treatment of disease. Science 267:1456–1462, 1995
4. Takamizawa S, Okamoto S, Wen J, et al: Differential apoptosis gene expression in pediatric renal tumors. J Pediatr Surg 35:390–395, 2000
5. Liston P, Roy N, Tamal K. Suppression of apoptosis in mammalian cells by NAIP and a related family of IAP genes. Nature 379:349–353, 1996

6. Deveraux Q L, Takaahashi R, Salvesen G S, et al: X-linked IA.P is a direct inhibitor of cell-death proteases. Nature 388:300–304–1997
7. Ambrosini G, Adid A, Altieri D: A novel anti-apoptosis gene, Survivin, expressed in cancer and lymphoma. Nat Med 3:917–921, 1997
8. Adida C, Berrebi D, Peuchmaur M, et al: Anti-apoptosis gene, Survivin, and prognosis of neuroblastoma (letter). Lancet 351:882–883, 1998
9. Swana H S, Grossman D, Anthony J, et al: Tumor content of the anti-apoptosis molecule Survivin and recurrence of bladder cancer. NEJM 341, 6:452–453,1999
10. Lu C-D, Altieri D C, Tanigawa N: Expression of a novel antiapoptosis gene, Survivin, correlated with tumor cell apoptosis and p53 accumulation in gastric carcinomas. Cancer Res 58;1808–1812,1998
11. Sandler A D, Okamoto S, Wen J, et al: Survivin in apoptosis and solid tumors of childhood. *Surg Forum* 50:571–572, 1999
12. Lowry O, Rosebrough N J, Farr A L, et al: Protein measurement with folinphenol reagent. J Biol Chem 193:265, 1951
13. Li F, Ambrosini G, Chu E, et al: Control of apoptosis and mitotic spindle checkpoint by Survivin. Nature 396:580–584, 1998
14. Li F, Ackerrnann E J, Bennett C F, et al: Pleiotropic cell division defects and apoptosis induced by interference with Survivin function. Nat Cell Biol 1:461–466,1999
15. Tamm I, Wang Y, Sausville E, et al: IAP-Family protein Survivin inhibits caspase activity and apoptosis induced by Fas (CD95), Bax, Caspases, and anticancer drugs. Cancer Res 58:5315–5320, 1998
16. Ashkenazi A, Dixit V. Death receptors: Signaling and modulation. Science 281:1305–1308, 1998
17. Brodeur G M, Castleberry R P. Neuroblastoma. In: Pizzo P A, Poplack D G, eds. Principles and practice of pediatric oncology. 3rd ed. Philadelphia: J B Lippincott, pp. 761–97, 1997.
18. Donaldson S A, Balmas Bourloud K, Beretta Brognara C, Hahne M, Tschopp J, Gross N. Expression of Fas/APO-1 by different clinical stages of human neuroblastoma. Proceedings of the American Association for Cancer Research 40:171, abstract 1141, 1999.

What is claimed is:

1. A diagnostic method for predicting the recurrence of a tumor or cancer in a human comprising:

(a) contacting RNA from a human physiological sample suspected of being tumorigenic or cancerous with a Survivin-specific oligonucleotide comprising a first label, and a pro-apoptosis factor (PAF)-specific oligonucleotide comprising a second label under conditions effective to hybridize the RNA to the oligonucleotides so as to yield a first population of RNA labeled with the Survivin-specific oligonucleotide and a second population of RNA labeled with the PAF-specific oligonucleotide;

(b) quantifying the first and second populations of labeled RNA to determine an amount of Survivin RNA and an amount of PAF RNA present in the sample; and (c) calculating the ratio of the amount of Survivin RNA and the amount of PAF RNA;

wherein a Survivin:PAF ratio of more than about 1.5 is predictive that the tumor will recur.

2. The method of claim 1, wherein the Survivin:PAF ratio of more than about 1.6 is predictive that the tumor will recur.

3. The method of claim 1, wherein the Survivin:PAF ratio of more than about 2.0 is predictive that the tumor will recur.

4. The method of claim 1, wherein the PAF is Fas, BID, p53, DR4, DR5, or TNF-R.

5. The method of claim 1, wherein the PAF is Fas.

6. The method of claim 1 wherein the physiological sample is a tissue sample.

7. The method of claim 6, wherein the tissue sample is a tissue-lysate protein sample.

8. The method of claim 6, wherein the tissue is from a solid tumor.

9. The method of claim 8, wherein the solid tumor is a childhood tumor.

10. The method of claim 9, wherein the childhood tumor is a Neuroblastoma, Pediatric renal tumor, Hepatoblastoma, Rhabdomysosarcoma, an undifferentiated sarcoma, a germ cell tumor, or an endocrine tumor.

11. The method of claim 8, wherein the solid tumor is an adult tumor.

12. The method of claim 11, wherein the adult tumor is a tumors of the nervous system, of the gastrointestinal or urogenital tract, or a sarcoma.

13. The method of claim 1 wherein the physiological sample is a fluid.

14. The method of claim 13, wherein the fluid is whole blood or blood serum.

* * * * *